US006494578B1

(12) United States Patent
Plummer et al.

(10) Patent No.: US 6,494,578 B1
(45) Date of Patent: Dec. 17, 2002

(54) VIRTUAL REALITY PERIPHERAL VISION SCOTOMA SCREENING

(75) Inventors: Daniel J. Plummer, San Diego, CA (US); Dirk-Uwe G. Bartsch, Del Mar, CA (US); William R. Freeman, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/615,222

(22) Filed: Jul. 13, 2000

(51) Int. Cl.$^7$ ................................................. A61B 3/02
(52) U.S. Cl. ...................................................... 351/224
(58) Field of Search ................................. 351/224, 225, 351/226, 221, 206, 239, 240, 243, 246

(56) References Cited

U.S. PATENT DOCUMENTS 3,883,235 A * 5/1975 Lynn et al. .................. 351/246
6,177,966 B1 * 1/2001 Masuda et al. ................. 349/8

OTHER PUBLICATIONS

Experimental Testing, Feb. 10, 1998–Sep. 30, 2001 at the Shiley Eye Institute, San Diego, CA.
Daniel J. Plummer, Ph.D., Ann Lopez, M.D., Stanley P. Azen, Ph.D., Laurie LaBree, M.S., Dirk–Uwe G. Bartsch, Ph.D., Alfredo A. Sadun, M.D., Ph.D., William R. Freeman, M.D., "*Correlation between Static Automated and Scanning Laser Entoptic Perimetry in Normal Subjects and Glaucoma Patients*", American Academy of Ophthalmology, vol. 109, No. 9, pp. 1693–1701, Sep. 2000.

Daniel J. Plummer, Ph.D., Alay Banker, M.D., Ibrahim Taskintuna, M.D., Stanley P. Azen, Ph.D., Pamela A. Sample, Ph.D., Laurie LaBree, M.S., William R. Freeman, M.D., "*The Utility of Entoptic Perimetry as a Screening Test for Cytomegalovirus Retinitis*", ARCH Ophthalmol, vol. 117, pp. 202–207, Feb. 1999.
Daniel J. Plummer, Ph.D., Stanley P. Azen, Ph.D., William R. Freeman, M.D., "*Scanning Laser Entoptic Perimetry for the Screening of Macular and Peripheral Retinal Disease*", ARCH Ophthalmol, vol. 118, pp. 1205–1210, Sep. 2000.

* cited by examiner

*Primary Examiner*—George Manuel
(74) *Attorney, Agent, or Firm*—Greer, Burns & Crain, Ltd.

(57) ABSTRACT

The invention utilizes a virtual reality display to present a random noise stimulus to a patient. Using an input device a patient indicates the location of disturbances in the random noise display. In a preferred embodiment, a scanning retinal laser projects the random noise stimulus directly onto a patient's eye(s). The image is preferably presented at virtual infinity and can be imaged over the peripheral retina. A patient is directed to centrally fixate on the random noise display. A visual aid, such as a cross hair, may be included in the generated display to facilitate this focus. With a scanning laser virtual reality device having a narrow exit, the failure of a patient to centrally fixate causes the image presented to be distorted, incomplete or disappear from view. While a patient views the random noise display, the patient is directed to indicate any areas of disturbance using an input device. A preferred input device is a computer pen and tablet. This is easy to use while also viewing the random noise display. Preferably, the display changes when a patient uses the pen and tablet such that the patient sees the location being indicated either in place of or superimposed upon the random noise display.

21 Claims, 1 Drawing Sheet

VIRTUAL REALITY PERIPHERAL VISION SCOTOMA SCREENING

FIELD OF THE INVENTION

The field of the invention is vision testing. In particular, the invention concerns screening for peripheral scotomas.

BACKGROUND OF THE INVENTION

Evaluation of a patient's vision typically relies upon a patient's ability to perceive normal visual stimulus. This limits diagnosis because patients experiencing peripheral visual field damage often remain visually asymptomatic. Patients often fail to notice any disturbance of the visual field until damage occurs close to the fovea. One of the most challenging problems in ophthalmology is the development of effective retinal screening tests for peripheral retinal disease.

Repression of pathologic blind or dark spots in a person's visual field, i.e., scotomas, is related to the Troxler phenomenon. In the Troxler phenomenon, a fixed spot of light above threshold presented to the peripheral visual field will disappear from view. This phenomenon applies primarily outside 12 degrees from fixation. This is likely due to neural mechanisms in the brain. The phenomenon is valuable to human vision in several respects. As an example, the Troxler phenomenon allows eye structures in a constant position in the visual field, e.g., blood vessels, to be repressed. It also permits most cortical function to remain focused on a centrally placed object of regard, except when peripheral items are moving or changing in luminosity. However, scotomas due to retinal injury or other pathology are also repressed by the Troxler phenomenon, and therefore are not perceived by patients being tested, especially if they are far from the fovea.

There are a large number of diseases which affect the peripheral retina which current screening methods are unable to detect with a high sensitivity (i.e., ocular melanoma, diabetic retinopathy, CMV retinitis, branch retinal vein occlusion). Early stages of glaucoma can exhibit such a repressed loss of peripheral visual field sensitivity producing wedge-like defects in the peripheral visual field. Left untreated, glaucoma often progresses to affect the central ten degrees of vision whereby patients then often become symptomatic. There are also diseases of the optic nerve (e.g., optic neuritis) and primary visual cortex (e.g., AVM producing homonymous hemianopias) which produce scotomas that are often repressed. Early detection of all diseases first affecting peripheral vision is accordingly essential for the prevention of severe vision loss.

The standard diagnostic tool to diagnose peripheral scotomas has been threshold perimetry. Entoptic, or snow-field perimetry, has been used to detect CMV retinitis, ocular melanoma, age-related macular degeneration, nonproliferative diabetic retinopathy, branch retinal occlusion, and other diseases with sensitivities and specificities over 95%. This technique uses a computer monitor filled with random particle motion. When the monitor is viewed by a person with normal vision, the screen appears as "visual noise". Subjects with peripheral retinal lesions are able to outline their scotomas. Those areas corresponding to the damaged retina appeared to have no random motion, and are described by patients as "gray" or "motionless" in appearance. The areas where patients perceive a lack of random particle motion correspond to retinal lesions.

Increasing the field of vision which may be tested using snow field perimetry requires larger computer screens and moving the patient as close as possible to the screen. Large screens require a large amount of space to use and store the equipment. Moving patients closer to the screen produces a distortion of the stimulus as people get close to the large screen (but outside the accommodative limit) while attempting to view the image in the peripheral retina. Patients, particularly geriatric populations who typically suffer from many of these diseases, are unable to accommodate well and cannot be placed close to screens to increase the stimulus size on the visual field. Furthermore, the screens suffer from poor contrast and a lack of lighting control. In addition, testing suffers from refractive and accommodative error correction.

Thus, there is a need for an improved peripheral scotoma screening diagnostic technique, and an improved device to aid such screening. The invention is directed to that need.

SUMMARY OF THE INVENTION

The present invention meets such a need. The invention utilizes a virtual reality display to present a random noise stimulus to a patient. Using an input device, a patient indicates the location of visual field disturbances in the random noise display. In a preferred embodiment, a scanning retinal laser projects the random noise stimulus directly onto a patient's eye(s). The image is preferably presented at virtual infinity and can be imaged over the peripheral retina (outside the central 10 degrees radius, where patients are typically asymptomatic). A patient is directed to centrally fixate on the random noise display. A visual aid, such as a cross hair, may be included in the generated display to facilitate this focus. With a scanning laser virtual reality device having a narrow exit pupil, the failure of a patient to centrally fixate causes the image presented to be distorted, incomplete or disappear from view. While a patient views the random noise display, the patient is directed to indicate any areas of disturbance using an input device.

A preferred input device is a computer pen and tablet. This is easy to use while also viewing the random noise display. Preferably, the display changes when a patient uses the pen and tablet such that the patient sees the location being indicated either in place of or superimposed upon the random noise display.

BRIEF DESCRIPTION OF THE DRAWINGS

Other features, objects and advantages of the invention will be apparent to those skilled in the art by reference to the detailed description and the drawings, of which.

DETAILED DESCRIPTION OF THE PREFERRED EMBODIMENTS

Figure 1:
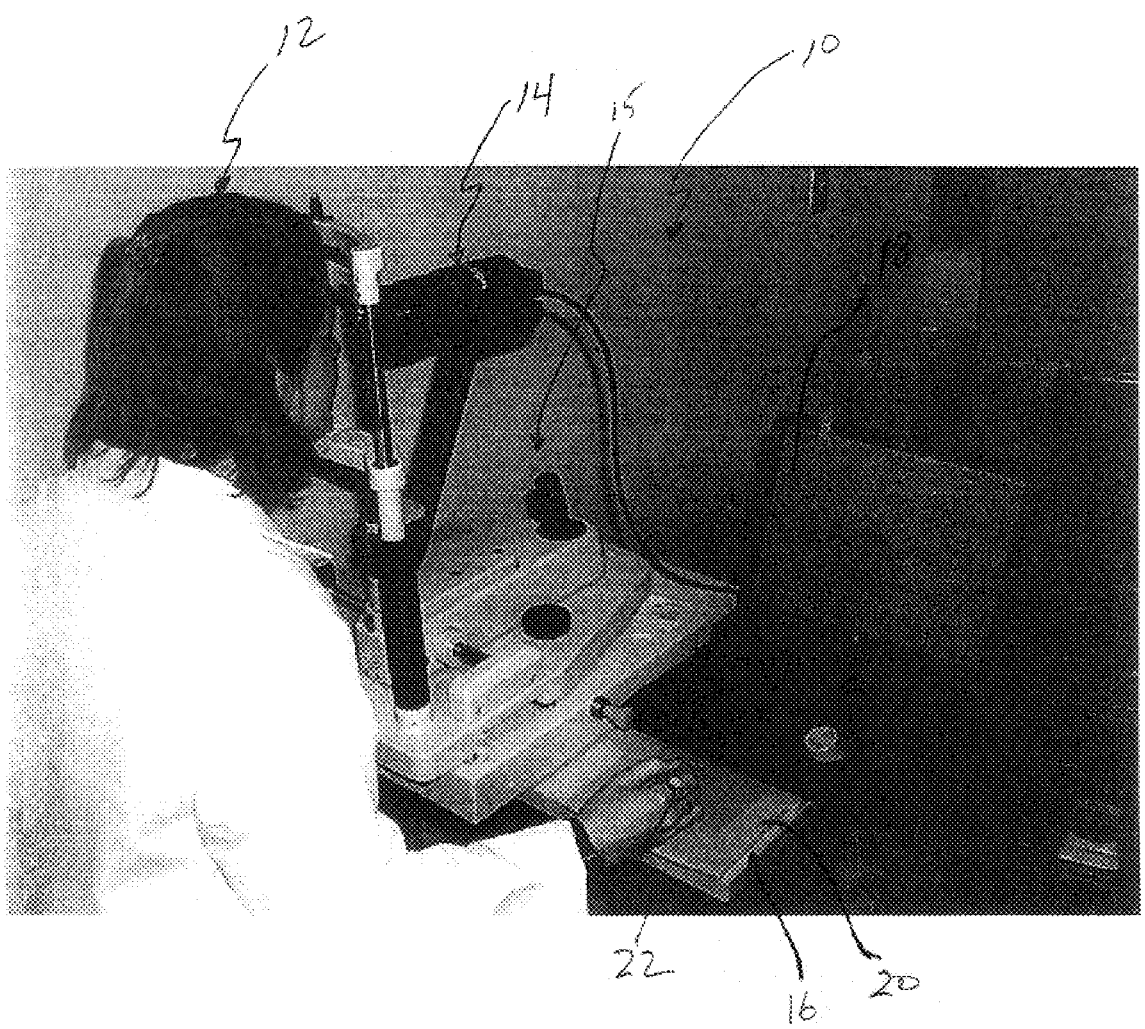
FIG. 1 is an illustration of a preferred scanning laser entoptic perimetry vision testing device according to the present invention.

Referring now to FIG. 1, shown is a vision testing device 10 constructed according to the present invention. A patient 12 is positioned to view a stimulus through a virtual reality display 14. A compact virtual reality display should be mounted on a suitable adjustable stand to 15 permit viewing by patients. A random noise stimulus is presented through the virtual reality display 14, and the patient is able to indicate any areas of apparent disturbance in the display using an input device 16. The device 10 may also include a standard display monitor 18 for a practitioner to monitor the images presented to the patient 12.

Preferably, the virtual reality display is a device to place images on a patient's eye(s) directly. A preferred display used in a prototype device of the invention is a retinal scanning laser display. A prototype used a Microvision Virtual Retinal Display™ system (VRD™) (Microvision Inc., Seattle, Wash., USA). The VRD™ projects images directly into the eye, at virtual infinity. The VRD™ images over the peripheral retina. This compensates for all but the most severe refractive errors. It also eliminates peripheral image distortion and the quality of the image allows for extremely high contrast. The scanning laser equipment is portable, easily fitting within a briefcase, allowing mobility within a clinical setting. A narrow exit pupil helps patients fixate centrally, reducing error rates due to inappropriate fixation. A computer tablet 20 and pen 22 are preferred for the input device 16. Such an input device is readily usable by a patient while viewing stimulus.

A controller, in the form of software, firmware or other code controls the virtual reality display 14 and the input device to run the display and input. With reference now to operation of a prototype for testing and diagnosis, artisans will recognize preferred operational features of the device and methods for its use. In a clinical study conducted at the Shiley Eye Center of the University of California at San Diego, the FIG. 1 device has been shown effective for diagnosis of peripheral scotomas.

Detection of Retinal Diseases

We recruited a total of 58 patients from the Shiley Eye Center and from the AIDS Ocular Research Unit at the University of California, San Diego. There was no requirement for visual acuity. A total of 110 eyes were tested using scanning laser entoptic perimetry. (Six patients had only one eye tested due to disease causing complete blindness in the fellow eye). All patients were recruited during ophthalmological visits for treatment or follow-up of ocular disease. Participation was entirely voluntary and we received informed consent.

STIMULUS

Scanning laser entoptic perimetry consisted of a monocular presentation on a VRD™ of monochromatic random particle motion. Each "pixel value" could be either on at 635 nm or off. The VRD™ delivered the entoptic stimulus through a narrow exit pupil (1 mm) which was then viewed by the subject.

The stimulus presented to the patient through the VRD™ was also "mirrored" by virtue of a video signal splitter which displayed the identical stimulus on a computer monitor. This allowed the experimenter to view the identical stimulus as the patient and control the entoptic perimetry program without interfering with the view of the patient in the VRD™.

PROCEDURES

Patients were initially dilated and received their ophthalmological examination and fundus photographs. Fundus photographs were taken to include all areas of retinal pathology. A diagram of lesion locations was made by a qualified ophthalmologist. Presence and locations of these lesions was confirmed by fundus photography, thereby effectively providing documentation of true location of any lesions on the retina within one hour of testing. In all cases, lesions observed by indirect ophthalmoscopy were in complete concordance with fundus photographs.

Next, patients were shown the computer monitor that mirrored the stimulus inside the VRD™, and were shown an example of the entoptic stimulus. Patients were given instructions on how to use the virtual pen. Patients were explained that they would view the identical stimulus (but for the red color) within the VRD™.

The entoptic program has two modes of display. The stimulus mode displays the entoptic stimulus. As the virtual pen was brought into close proximity to a touch-sensitive pad, the stimulus mode ended and the program entered the "recording" mode, where patients were presented with a blank workspace for drawing. The recording mode had several options. Placing the pen on the pad and moving it (keeping a firm, light pressure on the stylus) produced a black line against the background. Removing the pen from the pad but keeping it in close proximity to the pad (i.e., closer than 1 cm) allowed the patients to move the cursor on the screen without drawing. Pulling the pen away from the pad farther than 1 cm returned the viewer to the stimulus mode. Placing the pen close to the pad would again return the patient to the drawing screen, and previously drawn scotomas would remain. In this way, participants were able to turn the stimulus on and off under their own control. All actions were monitored by the technician who viewed the computer monitor during testing. This instructional phase rarely took longer than two minutes.

After instructions, patients were then seated in front of the VRD™ and asked to view the VRD™ with one eye (an eyepatch was provided). They were asked to fixate in specific locations within the visual field, and while remaining fixated, to report any perceptual changes.

Unlike computer monitors that can be viewed from a wide variety of angles, by virtue of the narrow exit pupil, patients had to concentrate on fixating within the VRD™ in order to see the entoptic stimulus. If their gaze wandered, the stimulus disappeared from view and they saw a black field. Thus, unless the patient was fixated centrally within the VRD™, patients were unable to see the stimulus.

SCREENING TO 120 DEGREES

The VRD™ we used had a capability for screening out to 30 degrees radius when the patient was fixated centrally upon a fixation crosshair. However, as there was no peripheral image distortion by having the patient fixate on the corners of the virtual screen, we placed crosshairs at the four corners of the screen as well as halfway along the vertical and horizontal edges of the screens. By having patients fixate on a corner of the virtual image (e.g., lower left), we were effectively able to screen out 60 degrees from fixation for a given quadrant. This procedure was repeated for the three other corners in a random order, therefore screening the entire central 120 degrees of the retina.

SCORING OPHTHALMOLOGIC FINDINGS

Presence or absence of retinal damage was determined by an expert ophthalmologist (WRF) using indirect ophthalmoscopy and confirmed by fundus photography. For each of the diseases listed in Table 1, we determined areas of damage to the retina using the following rules:

Diabetic Retinopathy, Branch Retinal Vein Occlusion.

Areas of nonperfusion and edema as seen with fluorescein angiography, confirmed by fundus photography. For each patient, there were also areas which had undergone panretinal laser photocoagulation.

CMV Retinitis.

Areas of retinal destruction by fundus photography seen as "healed" retinitis.

Ocular Melanoma.

Areas of the retina corresponding to the location of the tumor.

Macular Hole.

Areas relating to the hole and surrounding cuff of fluid.

AMPPE.

Areas of the RPE disturbed despite excellent visual acuity.

Age-related Macular Degeneration and Drusen.

Patients without laser surgery, both wet and dry, as confirmed by fundus photography.

Retinal Detachment/Tear.

Area of retinal detachment as confirmed by fluorescein angiography and fundus photography.

Toxoplasmosis.

Area of retinal sear as confirmed by fundus photography. The ophthalmologist also classified lesions as within the central 10 degrees (radius) of the visual field, between 10 and 30 degrees, from 30 to 60 degrees, or outside the central 60-degree radius, as measured from the fovea. The ophthalmologic examination was performed before entoptic perimetry testing.

SCORING PERIMETRIC FINDINGS

Presence or absence of entoptic perimetry visual field disturbance was determined by an expert psychophysicist (DJP). If a patient drew an area using the computer interface that corresponded to a localized change in the entoptic stimulus, the eye was classified as having a visual field disturbance. As with the ophthalmologic findings, we classified visual field disturbances as within the central 10 degrees (radius) of the visual field, between 10 and 30 degrees, from 30 to 60 degrees, or outside the central 60-degree radius, as measured from the fovea. The psychophysicist was masked to the outcome of the ophthalmologic findings.

STATISTICAL ANALYSIS

For each study eye, we computed the sensitivity, specificity, positive and negative predictive values of scanning laser entoptic perimetry. Sensitivity was calculated as the ratio of the number of eyes scored positive by scanning laser entoptic perimetry to the number of eyes scored positive by fundus photography. Specificity was calculated as the ratio of the number of eyes scored negative by perimetry to the number of eyes scored negative by fundus photography. Positive predictive value was calculated as the ratio of the number of eyes scored positive by scanning laser entoptic perimetry diagnosed as having retinal damage to the number of eyes with entoptic disturbances. Negative predictive value was calculated as the ratio of the number of eyes scored negative by scanning laser entoptic perimetry diagnosed as having retinal damage to the number of eyes without entoptic disturbances. We calculated these summary statistics for the following six regions: 1) lesions within the central 10 degrees radius (perimacular area), 2) within 30 degrees (SOCA Zone 1), 3) within 60 degrees, 4) from 10 degrees to 30 degrees, 5) from 30 degrees to 60 degrees, and 6) from 10 to 60 degrees (peripheral retinal imaging area).

RESULTS

A total of 58 patients (41 male, 17 female) underwent funduscopic examination and scanning laser entoptic perimetry testing for a total of I 10 eyes. Table I provides a breakdown of the numbers of patients and eyes in order of the frequency of diagnosis.

Table 2 summarizes the average (±SD) sensitivity and specificity stratified by retinal location along with both the positive and negative predictive values stratified by retinal location. Overall, we found that scanning laser entoptic perimetry had sensitivities ranging from 87% to 93% and specificities ranging from 91% to 100%, while positive predictive values range from 80% to 100% and negative predictive values from 89% to 97%. In particular, we found that scanning laser entoptic perimetry has a sensitivity of 93%±6%, a specificity of 100%±0%, a positive predictive value of 100%±0% and a negative predictive value of 89%±7% for detecting retinal lesions within the entire 120 degree visual field tested. Within the perimacular area (central 10 degrees radius of vision), where patients are usually symptomatic, we find that scanning laser entoptic perimetry had a sensitivity of 93%±9%, a specificity of 91%±6%, a positive predictive value of 80%±13% and a negative predictive value of 97%±5%. For those areas where patients generally remain asymptomatic to retinal lesions (i.e., from 10 degrees to 60 degrees radius from the fovea), scanning laser entoptic perimetry had a sensitivity of 92%±8%, a specificity of 95%±5%, a positive predictive value of 94%±7% and a negative predictive value of 94%±7%.

STIMULUS SIZE AND VISUAL ACUITY

As previously reported, the optimal sensitivity for patients with visual acuities 20/40 or better was obtained using a high-frequency Stimulus. However, we found that patients who have poor central visual acuity (e.g., 20/100 or less) often cannot perceive the fine stimulus. In this study, there were a total of 8 eyes that required a larger stimulus size in order to perceive the entoptic stimulus. For each of these cases, the patients had a poor central visual acuity. We performed sensitivity and specificity analyses using the minimum pixel size that the patients could perceive.

CASE REPORTS

The study cohort included one control patient with Behcet's disease but no retinal damage. Despite the opacification of the optic media, this patient was able to view the entoptic stimulus and reported no visual disturbances to the entoptic field.

The study cohort also included a patient who presented with a new retinal detachment (3 days). The detachment involved nearly the entire hemifield from the far periphery nearly up to the fovea. Upon viewing the stimulus, the patient clearly saw entoptic visual field disturbance extending into the far periphery. The following day the detachment was successfully repaired surgically. The patient underwent a vitrectomy without scleral buckle, had a long-acting gas injection and laser anterior to the equator to the retinal breaks. No procedures that would have caused retinal destruction occurred within the visual field. We tested the patient one day post-operatively (two days after the initial testing session) and despite the high refractive error introduced by the surgical procedure (due to the gas) the patient was able to view the entoptic stimulus (using a pixel stimulus size of 10) and found that the entoptic disturbance had disappeared. We followed this patient at bi-weekly intervals for a period of two months and found no further visual field disturbances, and the stimulus size required to perceive entoptic perimetry decreased with the reduction of the refractive error due to the decrease in size of the gas bubble. These follow-up visits were not included in the sensitivity/specificity analyses presented above.

Detection of Glaucoma

Using procedures identical to the previous study, we performed an experiment to determine the sensitivity and specificity of entoptic perimetry for the detection of visual field loss for all stages of glaucoma. As glaucoma is a disease of the optic nerve, the "gold standard" was not fundus photography nor fluorescein angiograms but visual field perimetry. Thus, the scoring procedures changed as follows:

SCORING VISUAL FIELD PERIMETRY FINDINGS.

Humphrey visual field printouts provide a series of measures which evaluate visual function. For this study, we evaluated the effectiveness of entoptic perimetry against the Humphrey Pattern Deviation (PD) plot. The PD performs an algorithm which "corrects" for diffuse loss due to cataracts from the total deviation (TD), which analyzes individual visual field locations for deviations from normal. In some cases, subjects can have a large number of points outside of normal limits on the TD plot, but appear relatively normal on the PD plot. In this study, we compared the sensitivity of entoptic perimetry against PD.

Scoring was performed as follows. Using the results of Humphrey visual field STATPAC printout, each of the 52 points tested during the 24-2 threshold algorithm were scored as either normal or abnormal. (The points directly above and below the blind spot were eliminated from the analysis, reducing the number from 54 to 52.) For both pattern deviation and total deviation, each point was classified as either normal or abnormal for four different conditions, representing scotoma severity: 1) a point was scored as abnormal if its sensitivity was 95% or more below of normal limits [all scotomas] 2) if sensitivity were 98% or more below normal limits [mild to severe scotomas] 3) if sensitivity were 99% or more below normal limits [moderate to severe scotomas] and 4) if sensitivity were 99.5% or more below normal limits [severe scotomas only]. This provided us with a progressive method for comparing entoptic perimetry tracings against visual fields with all types of defects [all scotomas] to only those with the most severe loss of sensitivity [severe scotomas only]. Normal limits were determined by the Humphrey STATPAC internal database.

Clinical Assessment of Sap

An ophthalmologist experienced in the treatment of glaucoma (AL) reviewed all Humphrey visual fields in a masked manner and assigned one of five classifications to each visual field (Normal, Suspect, Early, Moderate, Severe) based upon experience of diagnosing glaucoma. Based on the ophthalmologist's five classifications, we grouped patients into one of two groups, as either Normal/Suspect/Early or Moderate/Severe.

STANDARDIZED ASSESSMENT OF SAP

We grouped the subjects into two categories, as either Moderate/Severe or Normal/Suspect/Early based on clinical evaluation of the visual fields in either eye. We classified subjects into two categories, as either Normal/Early or Moderate/Sever. based on clinical evaluation using the Ocular Hypertension Treatment Study classification clinical evaluation of the automated Humphrey visual fields (Table 1, (Gordon, 1995 #225]).

RESULTS

Predictive Measures of Entoptic Perimetry vs. Sap Stratified by Category of Clinical Assessment Table 3 presents for each of the two categories the per-eye and per-subject sensitivity, specificity and percent correct classifications of entoptic perimetry for detecting glaucoma-related visual field defects.

In general, the sensitivity of entoptic perimetry was relatively high for subjects classified in the Moderate/Severe group (range=0.71 to 0.90), and increased with increasingly deeper scotomas, as reflected by greater levels of probability of abnormalities. Specificity was 1.00 for clinical assessment. In contrast, subjects classified as Normal/Early/ Suspect had low to moderate sensitivities (range=0.27 to 0.67). Specificity was adequate (range=0.78 to 1.00). For both sets of analyses, all measures tended to have more predictive power (as measured by percent correct) using the by-subject analyses and the pattern cluster analyses.

Predictive Measures of Entoptic Perimetry vs. Sap Using the Standardized Clinical Classification Table 4 presents for each of the two categories the per-eye and per-subject sensitivity, specificity, and percent correct classifications of entoptic perimetry for detecting glaucoma-related visual field defects. Results are similar to those given in Table 3, namely, sensitivities and specificities are relatively high for subjects classified in the Moderate/Severe group, and increase with increasingly deeper scotomas, represented by greater levels of probability of abnormalities. In contrast, subjects classified as Normal/Early have a relatively high specificity, but low to moderate sensitivity, despite the fact that the overall percentage correct remains the same. As with the Moderate/Severe group, predictive value also increases with the more severe scotomas. For both sets of analyses, all measures tend to have more predictive power using the by-subject analyses and the pattern cluster analyses.

SCANNING LASER ENTOPTIC PERIMETRY AS A GENERAL SCREENING DEVICE.

This study shows that scanning laser entoptic perimetry is sensitive and specific for screening for complete scotomas which are the result of retinal diseases. These results demonstrate that scanning laser entoptic perimetry is a viable possibility for a screening test to be administered by physicians, particularly primary care providers and in undeserved communities, where rapid, noninvasive screening procedures can be administered by support staff inexpensively. As entoptic perimetry screening takes less than one minute per eye, patients could potentially be routinely screened during annual physical checkups. This would not only allow asymptomatic patients with potentially sight-threatening diseases to be referred to ophthalmologists before central vision is impacted, early detection of diseases like ocular melanoma will allow early treatment before other organs are affected.

ANALYSIS BY LOCATION WITHIN THE RETINA.

In our previous studies with CMV retinitis we specifically did not include patients with central or optic nerve damage. One of the reasons for performing subgroup analyses within different regions based on distance from the fovea is that only the central portion of vision (within 10 degrees radius from the fovea) is affected in patients with diseases like macular holes, acute posterior multi focal placoid pigment epitheliopathy (AAVPE), and age-related macular degeneration and these patients, usually symptomatic, are artificially increasing our sensitivity. We maintained a sensitivity and specificity over 90% in our subgroup analyses which included only those areas where retinal damage would cause patients to generally remain asymptomatic (from 10' to 60' radius from the fovea).

This study of the present invention presents the first data using scanning laser entoptic perimetry to screen for lesions due to retinal disease outside the central 30' of vision. These results show that scanning laser entoptic perimetry of the invention is as sensitive and specific for the peripheral retina (from 30' to 60') as we previously demonstrated for the retina out to 30'. Further, this methodology of the invention requires no more time for screening, unlike current standard perimetric methods such as threshold perimetry.

ADVANTAGES OF THE INVENTION

Our previous studies demonstrated that, using a large computer monitor, we could screen the central 30-degree radius of vision rapidly and inexpensively. With the scanning retinal laser used as a virtual reality display, we have now demonstrated that scanning laser entoptic perimetry can screen for retinal disease with a high sensitivity and specificity within the central 120 degree diameter field of vision. This is a significant improvement over previous rapid screening methods such as the Amsler Grid, presenting the image over 75% more retinal area. Goldmann and Humphrey visual field perimetry can be used as screening tools for mapping of retinal scotomas out to 180 degrees from the fovea, but requires not only a significant investment in technicians and overhead for the provider, but also requires considerable time from the patient. As a result, the standard perimetric tests currently available are not good candidates for large-scale community-based screening programs.

Entoptic perimetry is not intended to replace the current uses of visual field perimetry, but instead can provide a valuable tool for the primary care provider in detecting retinal disease early. Furthermore, the preferred virtual reality display, the scanning retinal laser VRD™ is portable, and with optimization, could become part of school-based or other screening programs. The case reports we present also suggest that entoptic perimetry can be used by ophthalmologists to rapidly assess visual function in patients with opacities of the optic media which might prevent clear views of the retina, especially in cases like cataracts or vitritis. Furthermore, we were able to evaluate the success of retinal detachment repair patient who was tested both pre- and post-op. Despite the fact that the visual acuity was assessed as hand motion, the patient was able to see the entoptic stimulus and report that the previous visual disturbance had disappeared. Our diabetic patient who was able to view laser burns suggests that in screening tests, patients will be able to detect very small lesions throughout the visual field. These results warrant further detailed investigation.

This compensates for all but the most severe refractive errors, and also eliminates peripheral image distortion. The quality of the image allows for extremely high contrast. The scanning laser equipment is portable, easily fitting within a briefcase, allowing mobility within a clinical setting. A narrow exit pupil in our device ensured that subjects were fixated centrally, greatly reducing error rates due to inappropriate fixation.

We have recently demonstrated that the FIG. 1 device with a scanning retinal laser platform can be used to screen subjects for damage due to infectious retinopathies out of 60 degrees radius from the fovea. In this study, we found that scanning laser entoptic perimetry was able to detect visual field loss due to full-thickness retinal damage within the central 120 degrees (diameter) of vision with a sensitivity of 92%, specificity of 95%, positive predictive value of 94% and a negative predictive value of 94%. We present results evaluating the effectiveness of the VRD™ platform for screening for glaucomatous visual field defects.

The results of the clinical testing are presented in tables 1–4 below:

TABLE 1

Frequency Distribution and Diagnostic Description of Study Eyes

| Diagnosis | # patients w/diagnosis (n = 58) | # eyes w/ diagnosis (n = 80) | # companion eyes normal (n = 30) | # companion eyes not tested (n = 6) | sesnsitivity central 120° | specificity central 120° | average # lesions in eyes w/diagnosis | average # entroptic distrubances |
|---|---|---|---|---|---|---|---|---|
| CMV Retinitis* | 19 | 29 | 8 | 1 | 0.96 | 1.00 | 1.1 | 1.2 |
| Age-related Macular Degeneration | 9 | 14 | 3 | 1 | 0.86 | 1.00 | 1.0 | 1.0 |
| Retinal Detachment or Tear | 11 | 13 | 7 | 2 | 1.00 | 1.00 | 1.2 | 1.3 |
| Diabetic Retinopathy**** | 4 | 7 (1 with RD***) | 0 | 1 | 0.71 | — | 1 | 1 |
| Macular Hole | 4 | 4 | 4 | 0 | 1.00 | 1.00 | 1.0 | 1 |
| Branch Retinal Vein Occlusion | 3 | 3 | 3 | 0 | 1.00 | — | 1.3 | 1 |
| Ocular Melanoma | 3 | 3 | 3 | 0 | 1.00 | 1.00 | 1 | 1 |
| AMPPE** | 1 | 2 | 0 | 0 | 1.00 | — | 1 | 1 |
| Vitritis | 1 | 2 | 0 | 0 | — | 1.00 | 0 | 0 |
| Drusen alone | 2 | 2 | 1 | 1 | 1.00 | 1.00 | 1.5 | 2 |
| Non-HIV Related Toxoplasmosis | 1 | 1 | 1 | 0 | 1.00 | 1.00 | 1 | 1 |

*CMV = cytomegalovirus
**AMPPE = acute posterior multifocal placoid pigment epitheliopathy
***RD = retinal detachment
****as determined by areas of nonperfusion

TABLE 2

Average (±SD) Sensitivity, Specificity, Positive and Negative Predictive Values of Scanning Laser Entoptic Perimetry Stratified by Retinal Region

| Region | Sensitivity | Specificity | Positive Predictive Value | Negative Predictive Value |
|---|---|---|---|---|
| Within 20° diameter (peri-macular) | 93% ± 9% | 91% ± 6% | 80% ± 13% | 97% ± 5% |
| From 20° to 60° diameter | 90% ± 11% | 93% ± 5% | 81% ± 14% | 96% ± 6% |
| From 60° to 120° diameter | 87% ± 11% | 99% ± 2% | 89% ± 10% | 94% ± 8% |
| Within central 60° diameter | 90% ± 8% | 93% ± 6% | 92% ± 7% | 92% ± 8% |
| Within central 120° diameter | 93% ± 6% | 100% ± 0% | 100% ± 0% | 89% ± 7% |
| Between 20° to 120° diameter (peripheral) | 92% ± 8% | 95% ± 5% | 94% ± 7% | 94% ± 7% |

TABLE 3

Sensitivity, Specificity, and Predictive Value of Entoptic Perimetry by Clinical Classification of Severity
(number of moderate/severe subjects/eyes = 12/21;
number of normal/early/suspect subjects/eyes = 11/20)

| SAP | Sensitivity Moderate/Severe | Sensitivity Normal/Early Suspect | Specificity Moderate/Severe | Specificity Normal/Early Suspect | % Correct Moderate Severe | % Correct Normal/Early Suspect |
|---|---|---|---|---|---|---|
| Pointwise Deviation by eye | | | | | | |
| 95% | 0.71 | 0.27 | — | 1.00 | 71% | 45% |
| 98% | 0.75 | 0.50 | 1.00 | 1.00 | 76% | 80% |
| 99% | 0.75 | 0.40 | 1.00 | 0.87 | 76% | 75% |
| 99.5% | 0.75 | 0.50 | 1.00 | 0.88 | 76% | 80% |
| Cluster Deviation by eye | | | | | | |
| 95% | 0.75 | 0.25 | 1.00 | 0.81 | 76% | 70% |
| 98% | 0.83 | 0.33 | 1.00 | 0.82 | 86% | 75% |
| 99% | 0.83 | 0.33 | 1.00 | 0.82 | 86% | 75% |
| 99.5% | 0.83 | 0.50 | 1.00 | 0.83 | 86% | 80% |
| Pointwise Deviation by subject | | | | | | |
| 95% | 0.75 | 0.38 | — | 1.00 | 75% | 55% |
| 98% | 0.82 | 0.60 | 1.00 | 1.00 | 83% | 82% |
| 99% | 0.82 | 0.67 | 1.00 | 0.88 | 83% | 82% |
| 99.5% | 0.82 | 0.67 | 1.00 | 0.88 | 83% | 82% |
| Cluster Deviation by subject | | | | | | |
| 95% | 0.82 | 0.50 | 1.00 | 0.78 | 83% | 73% |
| 98% | 0.82 | 0.50 | 1.00 | 0.78 | 83% | 73% |
| 99% | 0.90 | 0.50 | 1.00 | 0.78 | 83% | 73% |
| 99.5% | 0.90 | 1.00 | 1.00 | 0.80 | 92% | 82% |

TABLE 4

Sensitivity, Specificity, and Negative Predictive Value of entoptic Perimetry by Standardized Classification of Severity
(number of moderate/severe subjects/eyes = 13/23;
number of normal/early/suspect subjects/eyes = 10/18)

| SAP | Sensitivity Moderate/Severe | Sensitivity Normal/Early | Specificity Moderate/Severe | Specificity Normal/Early/ | % Correct Moderate Severe | % Correct Normal/Early/ |
|---|---|---|---|---|---|---|
| Pointwise Deviation by eye | | | | | | |
| 95% | 0.65 | 0.31 | — | 1.00 | 65% | 50% |
| 98% | 0.68 | 0.67 | 1.00 | 1.00 | 70% | 89% |
| 99% | 0.67 | 0.75 | 0.50 | 0.93 | 65% | 89% |
| 99.5% | 0.67 | 1.00 | 0.50 | 0.93 | 65% | 94% |
| Cluster Deviation by eye | | | | | | |
| 95% | 0.67 | 0.67 | 0.50 | 0.87 | 65% | 64% |
| 98% | 0.74 | 1.00 | 0.75 | 0.88 | 74% | 91% |
| 99% | 0.74 | 1.00 | 0.75 | 0.88 | 74% | 100% |
| 99.5% | 0.78 | 1.00 | 0.75 | 0.88 | 78% | 100% |
| Pointwise Deviation by subject | | | | | | |
| 95% | 0.69 | 0.43 | — | 1.00 | 69% | 60% |
| 98% | 0.75 | 0.75 | 1.00 | 1.00 | 77% | 90% |
| 99% | 0.73 | 1.00 | 0.50 | 1.00 | 69% | 100% |
| 99.5% | 0.73 | 1.00 | 0.50 | 1.00 | 69% | 100% |
| Cluster Deviation by subject | | | | | | |
| 95% | 0.73 | 1.00 | 0.50 | 0.88 | 69% | 90% |
| 98% | 0.80 | 1.00 | 0.67 | 0.88 | 77% | 90% |
| 99% | 0.80 | 1.00 | 0.67 | 0.88 | 77% | 90% |
| 99.5% | 0.89 | 1.00 | 0.75 | 0.88 | 85% | 90% |

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. An entoptic perimetry vision testing apparatus comprising:
   a virtual reality display;
   an input device;
   a controller, said controller operating to produce a random particle motion display for display by said virtual reality display; to accept patient input from said input device; and to store, at least, positional data concerning the patient input; and
   wherein said apparatus has an enlarged field of view so that 120 degrees of a patient's retina may be scanned.

2. The apparatus according to claim 1, wherein said virtual reality display comprises a scanning laser retinal display device that projects images onto a patient's eye.

3. The apparatus according to claim 2, images presented by said scanning laser retinal display device are visible to a patient only when the patient's vision is centrally fixated.

4. The apparatus according to claim 2, wherein said scanning laser retinal display device presents the random particle motion display at virtual infinity.

5. The apparatus according to claim 4, wherein said controller presents a cursor in said random motion particle display in a orthogonal position corresponding to an orthogonal position on said electronic pad over which said electronic pen is positioned when said electronic pen is moved close to said electronic pad.

6. The apparatus according to claim 5, wherein said electronic pad displays an indication at an orthogonal position where said electronic pad is contacted by said electronic pen.

7. The apparatus according to claim 5, wherein said controller, when said electronic pen contacts said electronic pad, suspends said random motion particle display and displays a corresponding indication in a corresponding orthogonal location.

8. The apparatus according to claim 1, wherein said input device comprises an electronic pad and an electronic pen.

9. The apparatus according to claim 1, further comprising a monitor for displaying any image presented by the virtual reality display device.

10. An entoptic perimetry vision testing computer program for operating a vision test in an apparatus including a virtual reality display and an input device, the program comprising code for:

producing a random particle motion display on the virtual reality display;

accepting patient input from the input device;

storing, at least, positional data concerning the patient input; and providing an enlarged field of view so that 120 of a patient's retina may be scanned.

11. The program according to claim 10, wherein said producing, accepting, and storing are repeated, and said code for storing stores positional data concerning multiple patient inputs.

12. The program according to claim 10, further comprising code for suspending random particle motion display when the input device is active.

13. The program according to claim 12, further comprising code for presenting patient input accepted by said code for accepting on the virtual reality display while a patient is entering input to the input device.

14. A method of diagnosing retinal scotomas, the method comprising steps of:

having a patient view each of four corners of a random motion particle display presented by a virtual reality device having an enlarged field of view;

having the patient fixate vision on a central part of the random motion particle display;

having the patient indicate, using an input device, any orthogonal position in the random motion particle display having a disturbance;

noting the orthogonal position in which the patient perceives a disturbance in the random motion particle display; wherein a central 120 degrees of the patient's retina is screened.

15. An entoptic perimetry vision testing apparatus comprising:

a virtual reality display;

an input device; and a controller, said controller operating to produce a random particle motion display for display by said virtual reality display; to accept patient input from said input device; and to store, at least, positional data concerning the patient input;

wherein said virtual reality display comprises a scanning laser retinal display device that projects images onto a patient's eye.

16. The apparatus according to claim 15, images presented by said scanning laser retinal display device are visible to a patient only when the patient's vision is centrally fixated.

17. The apparatus according to claim 15, wherein said scanning laser retinal display device presents the random particle motion display at virtual infinity.

18. The apparatus according to claim 17, wherein said controller presents a cursor in said random motion particle display in a orthogonal position corresponding to an orthogonal position on said electronic pad over which said electronic pen is positioned when said electronic pen is moved close to said electronic pad.

19. The apparatus according to claim 18, wherein said controller, when said electronic pen contacts said electronic pad, suspends said random motion particle display and displays a corresponding indication in a corresponding orthogonal location.

20. An entoptic perimetry vision testing apparatus comprising:

a virtual reality display;

an input device;

a controller, said controller operating to produce a random particle motion display for display by said virtual reality display; to accept patient input from said input device; and to store, at least, positional data concerning the patient input; and wherein said electronic pad displays an indication at an orthogonal position where said electronic pad is contacted by said electronic pen.

21. An entoptic perimetry vision testing computer program for operating a vision test in an apparatus including a virtual reality display and an input device, the program comprising code for:

producing a random particle motion display on the virtual reality display;

accepting patient input from the input device;

storing, at least, positional data concerning the patient input; and wherein said producing, accepting, and storing are repeated, and said code for storing stores positional data concerning multiple patient inputs.

* * * * *

UNITED STATES PATENT AND TRADEMARK OFFICE
CERTIFICATE OF CORRECTION

PATENT NO.   : 6,494,578 B1
DATED        : December 17, 2002
INVENTOR(S)  : Daniel J. Plummer et al.

It is certified that error appears in the above-identified patent and that said Letters Patent is hereby corrected as shown below:

The title page should be deleted and substitute therefore the attached title page.

Signed and Sealed this

Nineteenth Day of August, 2003

JAMES E. ROGAN
*Director of the United States Patent and Trademark Office*

(12) United States Patent
Plummer et al.

(10) Patent No.: US 6,494,578 B1
(45) Date of Patent: Dec. 17, 2002

(54) VIRTUAL REALITY PERIPHERAL VISION SCOTOMA SCREENING

(75) Inventors: Daniel J. Plummer, San Diego, CA (US); Dirk-Uwe G. Bartsch, Del Mar, CA (US); William R. Freeman, Del Mar, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/615,222

(22) Filed: Jul. 13, 2000

(51) Int. Cl.$^7$ ............................................... A61B 3/02
(52) U.S. Cl. ..................................................... 351/224
(58) Field of Search .................................. 351/224, 225, 351/226, 221, 206, 239, 240, 243, 246

(56) References Cited

U.S. PATENT DOCUMENTS

| | | | |
|---|---|---|---|
| 3,883,235 A | * | 5/1975 | Lynn et al. ................. 351/246 |
| 6,177,966 B1 | * | 1/2001 | Masuda et al. ................. 349/8 |

OTHER PUBLICATIONS

Experimental Testing, Feb. 10, 1998–Sep. 30, 2001 at the Shiley Eye Institute, San Diego, CA.

Daniel J. Plummer, Ph.D., Ann Lopez, M.D., Stanley P. Azen, Ph.D., Laurie LaBree, M.S., Dirk-Uwe G. Bartsch, Ph.D., Alfredo A. Sadun, M.D., Ph.D., William R. Freeman, M.D., "*Correlation between Static Automated and Scanning Laser Entoptic Perimetry in Normal Subjects and Glaucoma Patients*", American Academy of Ophthalmology, vol. 109, No. 9, pp. 1693–1701, Sep. 2000.

Daniel J. Plummer, Ph.D., Alay Banker, M.D., Ibrahim Taskintuna, M.D., Stanley P. Azen, Ph.D., Pamela A. Sample, Ph.D., Laurie LaBree, M.S., William R. Freeman, M.D., "*The Utility of Entoptic Perimetry as a Screening Test for Cytomegalovirus Retinitis*", ARCH Ophthalmol. vol. 117, pp. 202–207, Feb. 1999.

Daniel J. Plummer, Ph.D., Stanley P. Azen, Ph.D., William R. Freeman, M.D., "*Scanning Laser Entoptic Perimetry for the Screening of Macular and Peripheral Retinal Disease*", ARCH Ophthalmol. vol. 118, pp. 1205–1210, Sep. 2000.

* cited by examiner

*Primary Examiner*—George Manuel
(74) *Attorney, Agent, or Firm*—Greer, Burns & Crain, Ltd.

(57) ABSTRACT

The invention utilizes a virtual reality display to present a random noise stimulus to a patient. Using an input device a patient indicates the location of disturbances in the random noise display. In a preferred embodiment, a scanning retinal laser projects the random noise stimulus directly onto a patient's eye(s). The image is preferably presented at virtual infinity and can be imaged over the peripheral retina. A patient is directed to centrally fixate on the random noise display. A visual aid, such as a cross hair, may be included in the generated display to facilitate this focus. With a scanning laser virtual reality device having a narrow exit, the failure of a patient to centrally fixate causes the image presented to be distorted, incomplete or disappear from view. While a patient views the random noise display, the patient is directed to indicate any areas of disturbance using an input device. A preferred input device is a computer pen and tablet. This is easy to use while also viewing the random noise display. Preferably, the display changes when a patient uses the pen and tablet such that the patient sees the location being indicated either in place of or superimposed upon the random noise display.

21 Claims, 1 Drawing Sheet

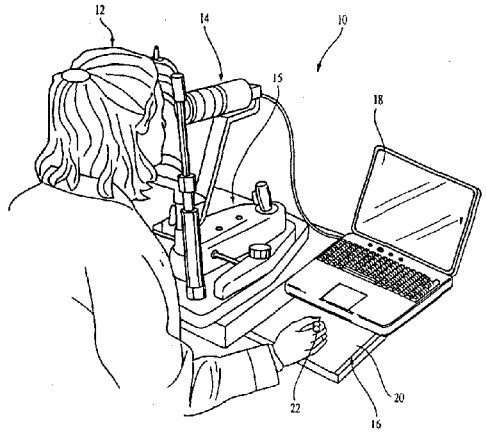

UNITED STATES PATENT AND TRADEMARK OFFICE
CERTIFICATE OF CORRECTION

PATENT NO.    : 6,494,578 B1
DATED         : December 17, 2002
INVENTOR(S)   : Plummer et al.

It is certified that error appears in the above-identified patent and that said Letters Patent is hereby corrected as shown below:

<u>Column 1,</u>
Line 2, please insert the following paragraph after the title of the invention at page 1, after line 1,
      -- STATEMENT OF GOVERNMENT INTEREST
   This invention was made with United States government assistance through NIH, Grant no. EY11961. The government has certain rights in this invention. --

Signed and Sealed this

Second Day of December, 2003

JAMES E. ROGAN
*Director of the United States Patent and Trademark Office*